(12) United States Patent
Clairaz et al.

(10) Patent No.: US 10,149,748 B2
(45) Date of Patent: Dec. 11, 2018

(54) SHEATHING FOR PACKAGING A PREDETERMINED VOLUME OF A BIOLOGICAL SUBSTANCE DESIGNED TO BE IMMERSED IN A LIQUID CRYOGENIC AGENT

(75) Inventors: Philippe Clairaz, Sceaux (FR); Anne-Linda Van Kappel, Lyons (FR); Francis Lesieur, Saint-Michel Thuboeuf (FR)

(73) Assignee: CRYO BIO SYSTEM, Saint-Ouen-sur-Iton (FR)

( * ) Notice: Subject to any disclaimer, the term of this patent is extended or adjusted under 35 U.S.C. 154(b) by 1858 days.

(21) Appl. No.: 12/088,506

(22) PCT Filed: Sep. 22, 2006

(86) PCT No.: PCT/FR2006/002172
§ 371 (c)(1),
(2), (4) Date: Mar. 28, 2008

(87) PCT Pub. No.: WO2007/036628
PCT Pub. Date: Apr. 5, 2007

(65) Prior Publication Data
US 2008/0233633 A1 Sep. 25, 2008

(30) Foreign Application Priority Data

Sep. 28, 2005 (FR) .................................... 05 09895

(51) Int. Cl.
*A01N 1/02* (2006.01)
*A61D 19/02* (2006.01)
*B01L 3/00* (2006.01)

(52) U.S. Cl.
CPC ............. *A61D 19/024* (2013.01); *A01N 1/02* (2013.01); *A01N 1/0268* (2013.01); *B01L 3/505* (2013.01);
(Continued)

(58) Field of Classification Search
CPC .................................................... A01N 1/0268
(Continued)

(56) References Cited

U.S. PATENT DOCUMENTS 3,212,207 A * 10/1965 Searing ........................... 40/316
4,134,359 A * 1/1979 Redpath ....................... 116/219
(Continued)

FOREIGN PATENT DOCUMENTS

DE 38 02 087 A1 7/1989
DE 10154431 A1 5/2003
(Continued)

OTHER PUBLICATIONS

Isachenko et al., "Aseptic technology of vitrification of human pronuclear oocytes using open-pulled straws", Nov. 3, 2004, Human Reproduction, vol. 20 No. 2, pp. 492-496.*
(Continued)

*Primary Examiner* — Jonathan M Hurst
(74) *Attorney, Agent, or Firm* — Browdy and Neimark, P.L.L.C.

(57) ABSTRACT

A sheathing for packaging a predetermined volume of a biological substance designed to be immersed in a liquid cryogenic agent, the sheathing including a thin tube and a ballast associated with the thin tube.

18 Claims, 4 Drawing Sheets

(52) U.S. Cl.
CPC ............... *B01L 2200/0689* (2013.01); *B01L 2300/0838* (2013.01)

(58) Field of Classification Search
USPC .................................................. 435/307.1
See application file for complete search history.

(56) References Cited

U.S. PATENT DOCUMENTS

| | | | |
|---|---|---|---|
| 4,761,314 A * | 8/1988 | Marshall ..................... | 428/11 |
| 5,036,904 A | 8/1991 | Kanda et al. | |
| 5,190,880 A | 3/1993 | Cassou et al. | |
| 5,545,562 A * | 8/1996 | Cassou et al. ............ | 435/307.1 |
| 6,303,285 B1 | 10/2001 | Woelders | |
| 6,332,822 B2 * | 12/2001 | Greenberg et al. ........... | 446/153 |
| 6,472,036 B2 * | 10/2002 | Saint-Ramon et al. ..... | 428/36.9 |
| 2004/0191754 A1 | 9/2004 | Meir et al. | |
| 2004/0259072 A1 * | 12/2004 | Kuwayama et al. .......... | 435/1.3 |
| 2005/0232813 A1 | 10/2005 | Karmali | |
| 2005/0247782 A1 * | 11/2005 | Ambartsoumian ........... | 235/385 |
| 2008/0220507 A1 | 9/2008 | Clairaz et al. | |

FOREIGN PATENT DOCUMENTS

| | | |
|---|---|---|
| EP | 0 480 109 A1 | 4/1992 |
| EP | 0 562 947 A1 | 9/1993 |
| EP | 0 635 305 A | 1/1995 |
| EP | 0 997 114 A1 | 5/2000 |
| WO | 9911121 A1 | 3/1999 |

OTHER PUBLICATIONS

Nakagata, "Cryopreservation of mouse spermatozoa", 2000, Mammalian Genome, 11, pp. 572-576.*
Kuleshova et al., "A strategy for rapid cooling of mouse embryos within a double straw to eliminate the risk of contamination during storage in liquid nitrogen", 2000, Human Reproduction, vol. 15 No. 12, pp. 2604-2609.*
Machine Translation of Cassou EP 0635305, Jan. 1995.*
Office Action dated Feb. 16, 2011, copending U.S. Appl. No. 12/088,638.
Copending U.S. Appl. No. 12/088,638, entitled "Kit for Packaging a Predetermined Volume of Substance to Be Preserved by Cryogenic Vitrification", filed Mar. 28, 2008.

* cited by examiner

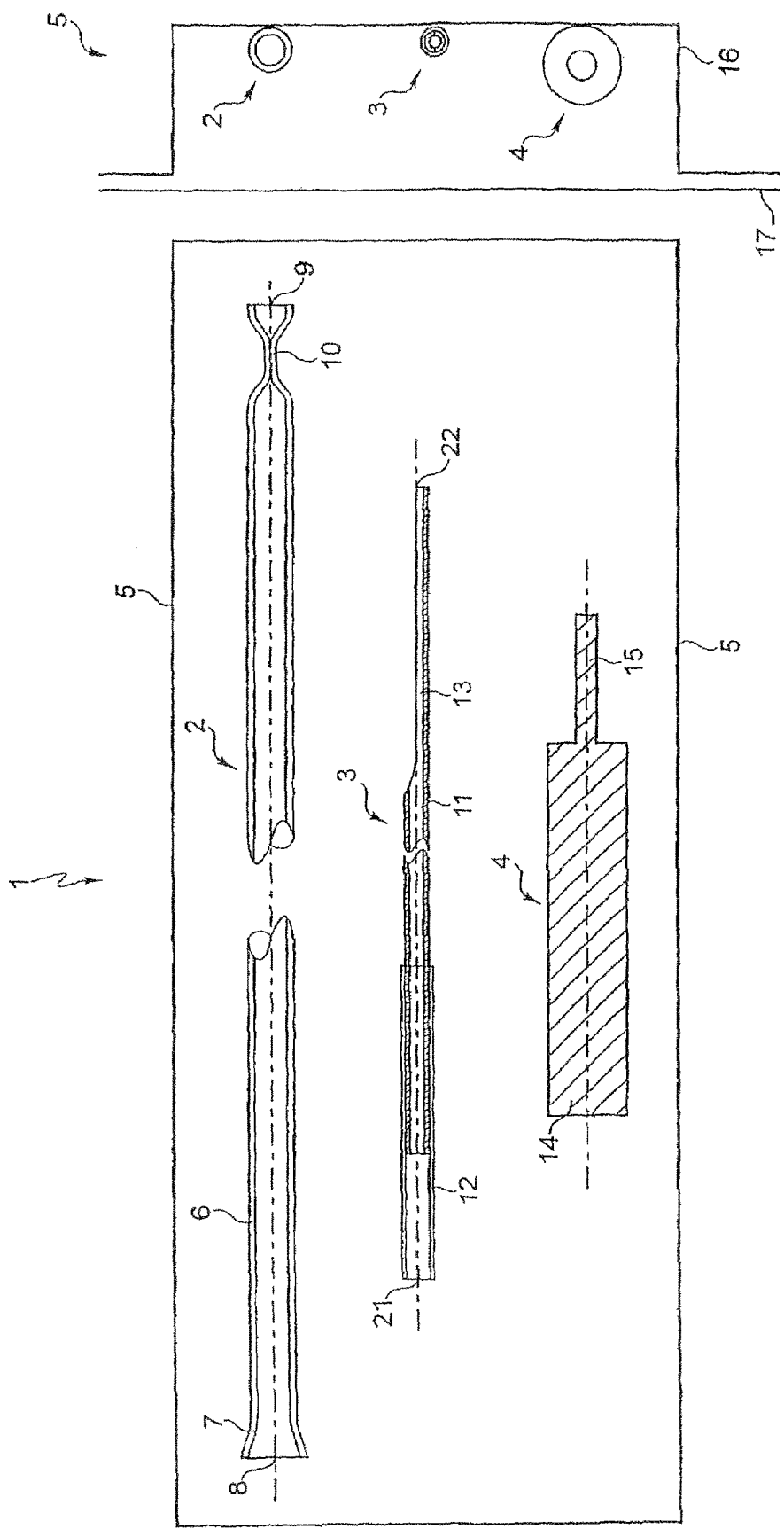

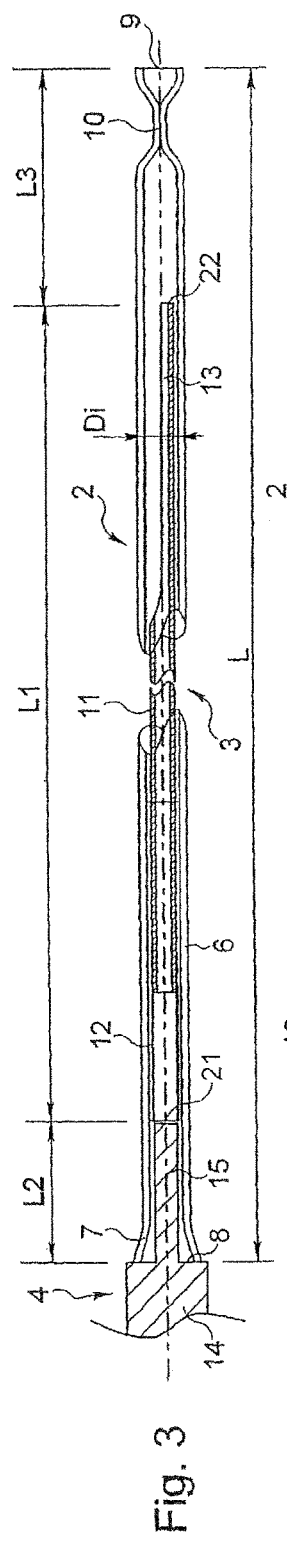
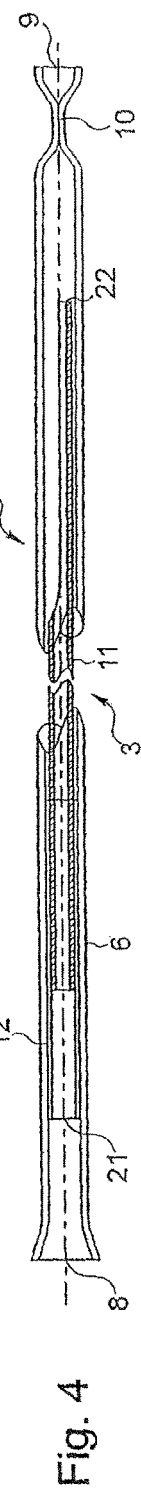
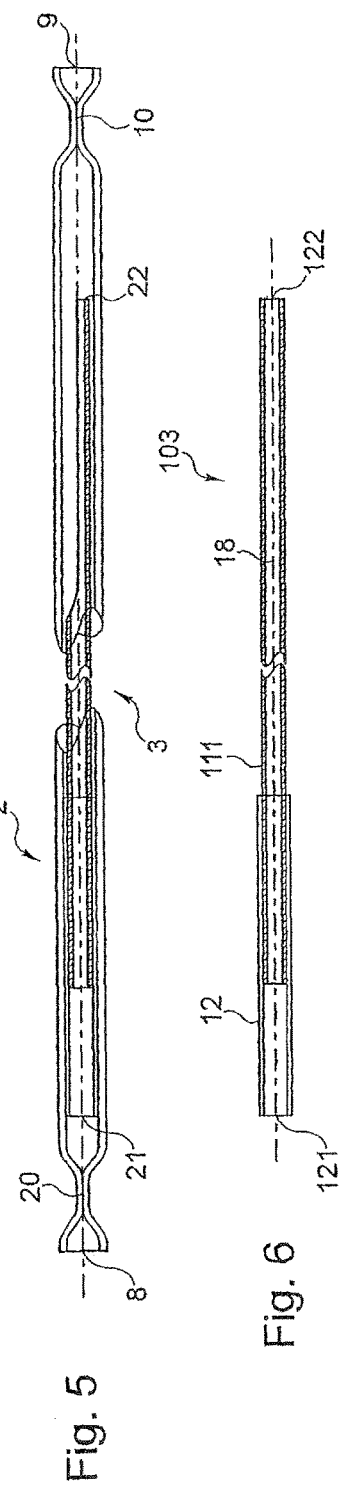
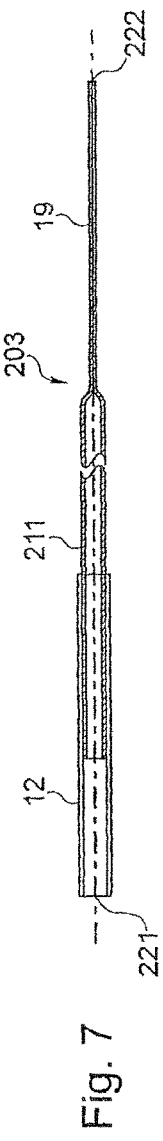
Fig. 3
Fig. 4
Fig. 5
Fig. 6
Fig. 7

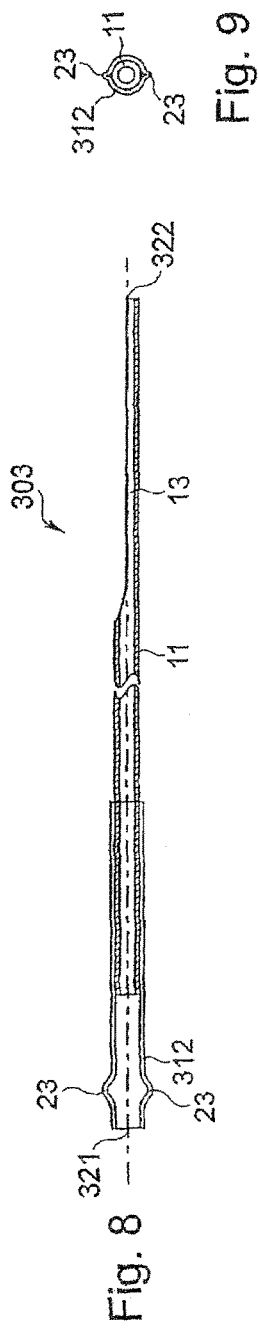
Fig. 8
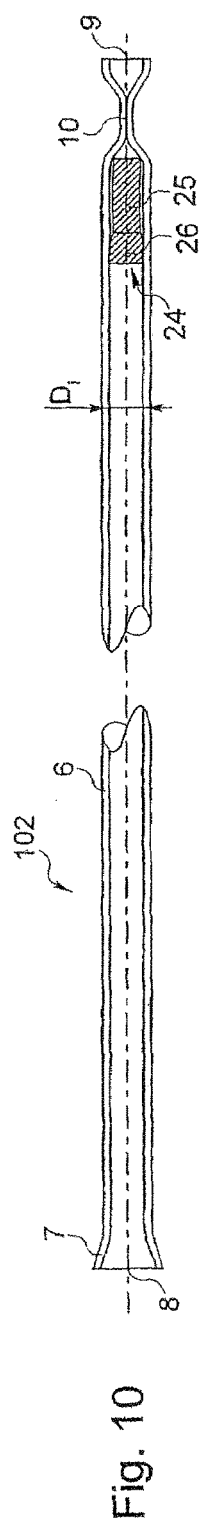
Fig. 9
Fig. 10
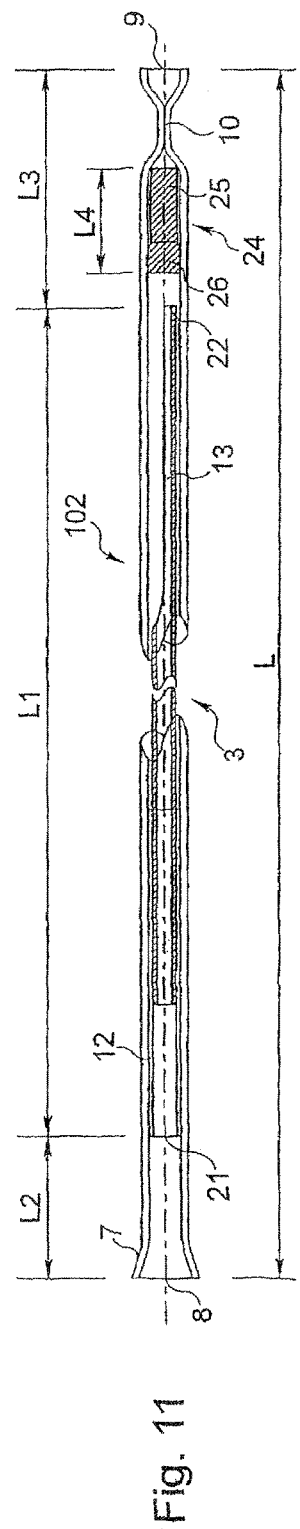
Fig. 11

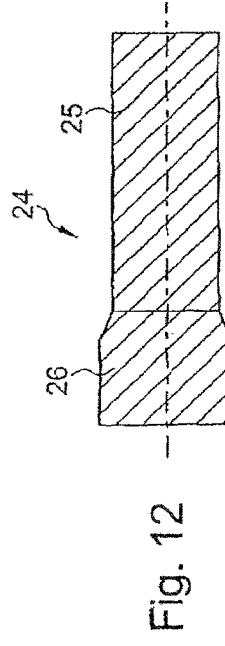
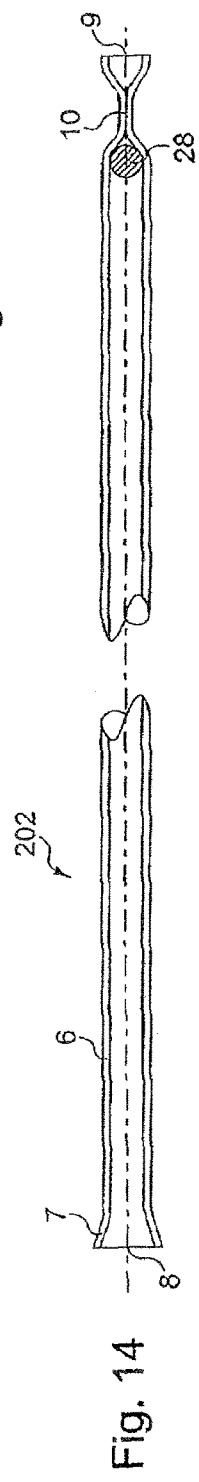
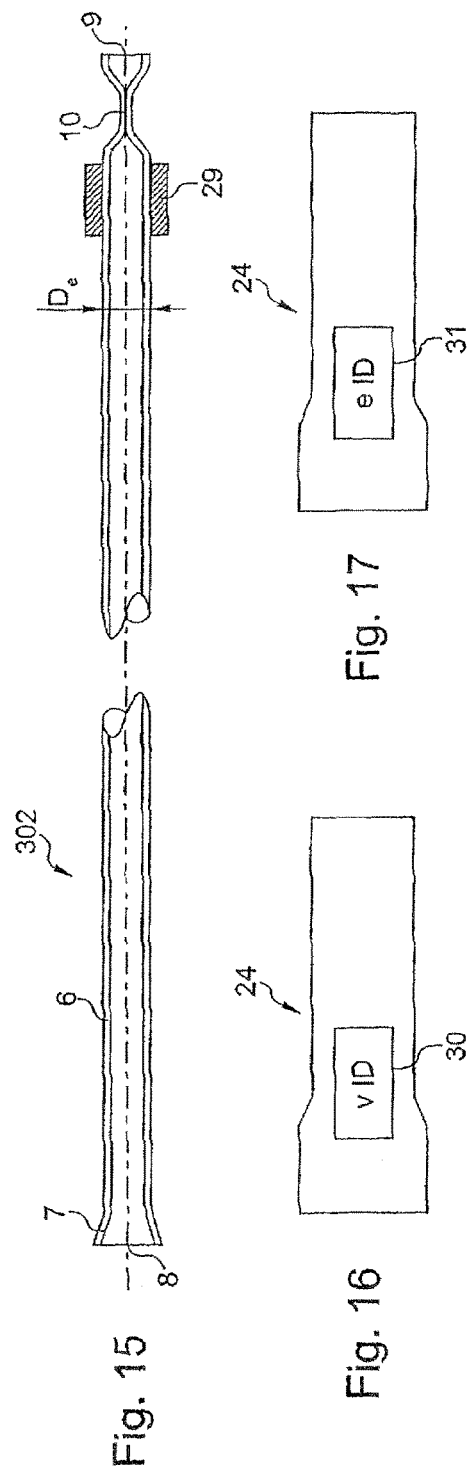
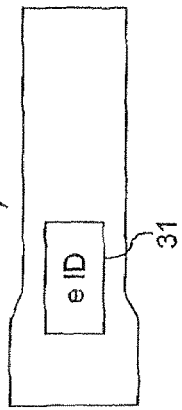
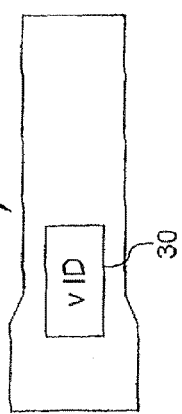
Fig. 12
Fig. 13
Fig. 14
Fig. 15
Fig. 16
Fig. 17

US 10,149,748 B2

SHEATHING FOR PACKAGING A PREDETERMINED VOLUME OF A BIOLOGICAL SUBSTANCE DESIGNED TO BE IMMERSED IN A LIQUID CRYOGENIC AGENT

BACKGROUND OF THE INVENTION

The present invention concerns sheathing for packaging a predetermined volume of a biological substance intended to be immersed in a liquid cryogenic agent.

Sheathings are known formed of a thin tube in which is stored a liquid substance to be preserved, in particular for sample preservation, for example by the "vitrification" method, which consists in cooling the substance to be preserved quasi-instantaneously by immersing the sheathing and the biological substance that it contains in a liquid cryogenic agent (for example liquid nitrogen).

Once the biological liquid substance has been introduced into the thin tube, the sheathing is sealed at both ends by heat welding to seal it for subsequent immersion in the liquid nitrogen.

SUMMARY OF THE INVENTION

The invention aims to provide sheathing for packaging of the same type that is more convenient and simple to use.

To this end it proposes sheathing for packaging a predetermined volume of a biological substance intended to be immersed in a liquid cryogenic agent, including a thin tube, characterized in that it further includes a ballast weight associated with said thin tube.

The integration of a ballast weight into the sheathing enables the sheathing to be immersed efficiently in the liquid nitrogen and prevents residual air contained in the sheathing from causing it to float, as a result of which cooling of the biological substance is effected homogeneously and quasi-instantaneously.

According to features that are preferred, for the same reasons as explained hereinabove:
said ballast weight is disposed inside said thin tube; and, where applicable
said ballast weight is a slug including a round cross section first portion and an oval cross section second portion; and/or
said ballast weight is a ball; and/or
said thin tube has a welded portion against which said ballast weight abuts; and/or
there exist between said ballast weight and said thin tube holding means for holding said ballast weight in said thin tube at a predetermined position; and, where applicable
said holding means include at least one projecting portion of said ballast weight; and/or
said ballast weight is disposed around said thin tube; and, where applicable
said ballast weight is a ring; and, where applicable
said thin tube has a predetermined outside diameter and said ballast weight has a predetermined inside diameter less than said outside diameter of said thin tube thanks to which said ballast weight is held in place by deforming said thin tube; and/or
said ballast weight is disposed at one end of said thin tube; and/or
said ballast weight is made of metal; and/or
means for identifying said biological substance are associated with said ballast weight; and, where applicable
said identification means are visual; and/or
said identification means are electronic.

BRIEF DESCRIPTION OF THE DRAWINGS

The features and advantages of the invention will emerge from the following description of a preferred example, given by way of nonlimiting illustration, with reference to the appended drawings, in which:

FIG. 1 is an enlarged view in longitudinal section showing sheathing including a thin tube suitable for cooperating with a ballast weight in accordance with the invention, a support and a plunger of a packaging kit disposed in a unitary packaging;

FIG. 2 is a similar view in cross section;

FIG. 3 is a view in section showing the positioning of the sheathing, the support and the plunger of this kit at the end of the operation of introducing the support into the sheathing;

FIG. 4 is a view similar to FIG. 3 but in which the plunger has been withdrawn;

FIG. 5 is a view similar to FIG. 4 but in which the sheathing is welded at both ends;

FIGS. 6 and 7 are views in section respectively showing second and third embodiments of the support of the packaging kit;

FIGS. 8 and 9 are respectively a view in section and a view in elevation from the side that is seen on the left in FIG. 8 of a fourth embodiment of the support of the packaging kit;

FIG. 10 is a view in section of sheathing according to the invention, including the thin tube shown in FIGS. 1 to 5 and a ballast weight disposed in the thin tube;

FIG. 11 is a view in section similar to FIG. 10 but showing the positioning of the support in this sheathing at the end of the operation of introducing the support into the sheathing;

FIGS. 12 and 13 are respectively a view in section and a view in elevation from the side that is seen on the left in FIG. 12 of the ballast weight that this sheathing includes;

FIGS. 14 and 15 are two views in section showing two embodiments of the sheathing for which the ballast weight is conformed differently; and FIGS. 16 and 17 are two diagrammatic views of ballast weights associated with means for identifying the biological substance, visual means in one case and electronic means in the other.

DETAILED DESCRIPTION OF THE INVENTION

The present specification describes for convenience, with reference to FIGS. 1 to 5, sheathing with no ballast weight, but it is to be understood that sheathing according to the invention includes a ballast weight, as shown in FIG. 10 et seq.

The packaging kit 1 represented in FIG. 1 is intended to package a predetermined volume of substance to be vitrified, for which purpose it includes the sheathing 2, a support 3 and a plunger 4.

The kit 1 is contained in a unitary packaging 5.

The sheathing 2 shown in FIGS. 1 to 5 includes a thin tube 6 of length L and of inside diameter Di (FIG. 3). The thin tube 6 has a flared portion 7 at a first end 8 and a weld 10 in the vicinity of the opposite end 9.

It will be noted that the term "weld" is used interchangeably here to designate either the welded area as such or the welded area and the deformed portion that surrounds it.

The sheathing 2 is made of a polymer material chosen for example from ionomer resins for their high mechanical strength, their behavior at low temperature and their capacity to be welded easily whilst providing a good seal.

Ionomer resins, formed by associating a copolymer of ethylene and a carboxylic acid with a metallic cation having the property of behaving, above a transition temperature zone, situated in the range 40° C.-90° C., like a thermoplastic material, whereas below that transition zone they behave like a cross-linked material, the metallic cations cross-linking linear copolymer chains. The transformation is reversible. Welding the tube is simple and effective, above the transition temperatures; cooling after welding induces few internal stresses, the fixing of the resin by ionic cross-linking not being accompanied by significant variations of volume.

These resins are sold under the trademark Surlyn®.

At ambient temperature the cross-linked structure of Surlyn® resins gives the sheathing good mechanical strength; the sheathing does not tend to creep under its own weight and remains straight.

Surlyn® resins of course have appropriate qualities of transparency and biological neutrality.

The resin employed here is of the type sold under the name Surlyn® 8921 (also known under the Surlyn® product reference "PC100"). This resin includes a sodium metallic cation and it has not been possible to determine a weakening temperature for it. In relation to the transition zone, the melting point is 84° C. and the solidification point is 52° C.

The welding is effected in the range 90° C.-110° C.

In the example shown, the wall of the thin tube 6 has a thickness between 0.125 and 0.300 mm and an inside diameter between 0.95 and 2.55 mm (1.60 mm in the example shown) for a length of 133 mm. The flare 7 extends over a length of 1.5 mm.

The support 3 consists of an elongate tubular portion 11 nested coaxially inside a tubular end-piece 12 with an outside diameter greater than that of the tubular portion 11 so as to obtain a staggered support of length L1 (FIG. 3).

Here the tubular portion 11 is cut away over an angle of about 180° and over a distance of about 15 mm from the end opposite that nested inside the end-piece 12 to form a trough 13 which, as explained hereinafter, constitutes the zone for receiving the predetermined volume of substance.

The tubular end-piece 12 is a tube with an outside diameter less than the inside diameter Di of the sheathing.

The end-piece 12 is colored, one color corresponding to one type of biological substance, for example.

The unitary packaging 5 and the tubular end-piece 12 also carry alphanumeric and/or bar code type markings (not shown in the figures) for identifying the packaging kit 1.

As explained hereinafter with reference to FIG. 3, the support 3 has a maximum transverse dimension less than the inside diameter Di of the thin tube and a length L1 less than the length L of that tube so that it can be introduced into the sheathing 2 with a gap remaining between each end 21 and 22 of the support 3 and the corresponding adjacent end 8, 9 of the thin tube 6 for welding the thin tube in the vicinity of the two ends when the support 3 is in a globally centered position inside the tube 6.

Here the end-piece 12 and the tubular portion 11 are made from PETG.

The plunger 4 and the packaging 5 are described next with reference to FIGS. 1 to 3.

The plunger 4 has a first cylindrical portion 14 with an outside diameter greater than the inside diameter Di of the tube 6 and a second cylindrical portion 15 having an outside diameter less than the inside diameter Di of this tube. The second cylindrical portion has a length L2 (FIG. 3).

The packaging 5 is a peelable tray, here made of Tyvek®, having an area 16 for receiving each of the components of the packaging kit disposed side by side (namely the sheathing 2, the support 3 and the plunger 4) sealed by a peelable film 17.

The operation of packaging the volume to be preserved is described next with the aid of FIGS. 1 to 5.

The operator opens the packaging 5 by peeling off the film 17 to access the support 3 and pick it up by the manipulation end piece 12. A volume of liquid substance (not shown in the figures) is then deposited by the operator in the trough 13 of the support 3.

The support 3 is then introduced into the thin tube 6 of the sheathing 2, the trough 13 first, through the end 8. The flared portion 7 facilitates guiding the support 3 toward the interior of the tube.

The plunger is then placed in front of the end 8 of the tube 6 to introduce the portion 15 therein. The staggered shape of the plunger 4 and its dimensions enable introduction of the portion 15 without the portion 14 entering, the shoulder that the portion 14 comprises at its junction with the portion 15 forming an abutment that comes up against the edge of the flare 7.

In this abutment position shown in FIG. 3, the support 3 has been pushed into the thin tube 6 of a length equal to the length L2 of the portion 15.

In this position, the support 3 is globally centered in the tube 6 with a gap between each of its ends 21, 22 and the respective adjacent ends 8, 9 of that tube.

Once the plunger has been withdrawn, the gap between the end 21 of the support 3 and the adjacent end 8 of the thin tube 6 is sufficient for a weld 20 to be produced easily in the end portion of the tube of length equal to L2 (FIG. 5).

Similarly, weld 10 has already been produced in the opposite end portion of the thin tube 6 of length L3 equal to the difference between the length L of the tube 6 and the sum (L1+L2) of the length L2 of the portion 15 and the length L1 of the support 3.

The gap between the end 22 of the support 3 and the end 9 of the tube 6 is sufficient for the support 3, with the weld 10 already executed, to be introducible into the interior of the tube to a length at least equal to the sum (L1+L2) of the length L2 of the portion 15 and the length L1 of the support 3 without the support being impeded by the weld 10.

In this example, the length L2 is 8 mm.

The tubular end-piece 12 places the trough 13 coaxially at the center of the tube 6 to avoid any contact of the substance to be vitrified with the internal surface of this tube.

The plunger 4 is individual to each packaging kit and is disposable in order to minimize the risk of contamination during packaging.

The sheathing 2 containing the support 3 and welded at both ends is then immersed vertically, to facilitate storage, in a cryogenic liquid (for example liquid nitrogen) to vitrify the substance with a view to its cryopreservation.

When the sheathing 2 is immersed vertically, the substance (liquid prior to freezing) does not flow because of the viscosity of the cryoprotectors that constitute it and that are the source of surface tensions with the support 3 sufficiently high to prevent the drop from flowing.

The support 3 can be replaced by the supports 103, 203 and 303 shown in FIGS. 6, 7 and 8, respectively. As a general rule, there have been retained for exactly identical elements the same reference numbers as for the support 3, whereas for similar elements the same reference numbers are used but increased by 100 for each embodiment.

The support 103 shown in FIG. 6 has a tubular portion 111 that is not open in the manner of a trough at its end, the liquid substance then being aspirated by capillary action or by generating a reduced pressure (by means of a vacuum supply, for example) applied to the end 121 of the support 103. The liquid substance then enters via the end 122 to occupy a portion of the internal volume 18 of the tubular portion 111.

The support 203 shown in FIG. 7 has a 15 mm crushed tubular portion 211 forming a flat 19 that constitutes the reception area on which the volume of liquid substance is deposited.

In the support 303 represented in FIGS. 8 and 9, the tubular end-piece 312 has two diagonally opposite bosses 23. The bosses are obtained by crushing the material locally to increase the maximum transverse dimension of the support 303 so as to be slightly greater than the inside diameter Di of the thin tube 6. In this way, when the support 303 is introduced into the thin tube 6, the crushed portions 23 come to bear against the internal surface of the thin tube 6 of the sheathing 2, locally deforming the thin tube 6 to act like a positioning brake and to hold the support 303 in position, preventing any unintentional sliding movement of the support 303 inside the sheathing 2 under its own weight.

In the example shown the formation of the bosses by crushing increases the maximum transverse dimension of the support from 1.4 to 1.7 mm.

In variants that are not shown, the bosses 23 are replaced by bosses formed on the thin tube 6 of the sheathing and projecting inward to reduce the inside diameter of the tube 6 locally or are replaced by one or more projections other than a simple boss.

The support can also have dimensions such that it is a snug sliding fit in the sheathing.

The sheathing 2 can be replaced by the sheathings 102, 202 and 302 shown in FIGS. 10, 14 and 15, respectively. Each of these sheathings includes a ballast weight cooperating with the thin tube.

The sheathing 102 shown in FIG. 10 therefore includes in addition to the thin tube 6 a ballast weight disposed inside the thin tube 6.

The ballast weight is a slug 24 having a first portion 25 with a round section and a second portion 26 crushed to an oval section. A portion of the section 26 delimited by the surface 27 projects relative to the portion 25. This slug is made from a material of greater density than the cryogenic liquid agent, metal in the example shown.

The oval cross section portion 26 has a maximum transverse dimension slightly greater than the inside diameter Di of the thin tube 6 in order for the projecting portion, during the operation of introduction of the slug 24 into the sheathing 2, to come to bear against the internal surface of the thin tube 6, deforming the thin tube 6 locally to act like a positioning brake and to retain the slug 24 by preventing any unintentional sliding movement of that slug under its own weight inside the thin tube 6.

The operation of introduction of the slug 24 into the thin tube 6 is described next with the aid of FIGS. 10 and 11.

The slug 24 is introduced into the thin tube 6 before the weld 10 is executed, with a gap remaining between the ballast weight 24 and the end 9 of the tube 6.

Once the slug has been introduced, the weld 10 is produced in the end portion of the thin tube 6 situated between the end 9 and the slug 24.

The slug is then pushed by means of a rod (not represented in the figures) introduced via the end 8 so that it comes to abut against the weld 10 of the thin tube 6 as shown in FIG. 10.

The slug 24 has dimensions such that it can abut against the weld 10 in the space situated between the end 22 of the support 3 (once this has been introduced into the sheathing and placed in position with the aid of the plunger 4) and the weld 10 with a gap remaining between it and the end 22.

In this example, the ballast weight has a length L4 of 10 mm, the gap between the end 21 of the support 3 and the adjacent end 8 of the tube 6 is 8 mm, and the gap between the opposite end 22 of the support 3 and the ballast weight 24 is 5 mm.

This ballast weight tends to cause the sealed sheathing to be immersed vertically in the liquid nitrogen, thus preventing air trapped in the sheathing and causing it to float on the surface of the liquid nitrogen.

The sheathing is therefore surrounded very quickly and over the whole of its surface with liquid nitrogen, and the biological substance is then vitrified homogeneously and quasi-instantaneously.

The ballast weight situated at the end of the thin tube 6 does not interfere with the cooling of the substance to be vitrified.

This quasi-instantaneous and homogeneous cooling of the biological substance ensures vitrification of a quality that minimizes the risks of destruction of the microorganisms or cells present in the biological substance.

In the sheathing 202 shown in FIG. 14, the ballast weight is a metal ball 28 of diameter slightly greater than the inside diameter Di of the thin tube 6. The ball 28 is disposed in the thin tube 6 against the weld 10 by the same method as described for introduction of the slug 24 into the thin tube 6.

In the case of a ballast weight disposed inside the thin tube, two welds such as the welds 10 can be produced on respective opposite sides of the ballast weight to prevent any contact with the biological substance (for example if the biological liquid substance is poured directly into the internal volume of the tube 6).

An alternative is to use an annular ballast weight like that represented in FIG. 15. The ballast weight of the sheathing 302 is a metallic ring 29 threaded around the thin tube 6. The ring 29 has an inside diameter slightly less than the outside diameter De of the thin tube 6 in order for the ring 29 to bear against the external surface of the thin tube 6 and deform the tube locally.

In the embodiments represented in FIGS. 16 and 17, means for identifying the biological substance that the thin tube contains are associated with the ballast weight 24. The identification means 30 represented in FIG. 16 are visual and consist of a color code, a bar code or a string of characters.

The identification means 31 represented in FIG. 17 are electronic, for example an RFID microchip or an electromagnetic patch stuck to the ballast weight or integrated into it.

In embodiments that are not represented, the ballast weights 28 and 29 include identification means such as the means 30 or 31 and/or the sheathing includes an identification sleeve around the thin tube 6.

It is possible to replace the ballast weight 29 by a ballast weight also disposed outside the thin tube 6 but surrounding the weld 10 once the latter has been made, for example.

It is equally possible to combine any of the sheathings with any of the supports described hereinabove.

Whichever embodiment is chosen, the weld 10 can be made only once the support has been introduced into the sheathing and placed in position with the aid of the plunger 4.

The invention also concerns all types of ballasted sheathing for packaging intended to be immersed in a conservation liquid agent.

The present invention is not limited to the embodiments described and shown and encompasses any variant execution thereof.

The invention claimed is:

1. A kit for packaging a predetermined volume of a biological substance, said kit comprising:

a sheathing configured to be immersed in a cryogenic agent, including a thin tube having two opposed ends and an inside diameter, and a support including a zone for receiving said predetermined volume, said support being configured to be introduced into said thin tube and having a maximum transverse dimension less than the inside diameter of said thin tube, wherein said sheathing further includes a ballast weight associated with said thin tube only at one end of said sheathing, further wherein said thin tube, said ballast weight and said support are configured so that, after said kit is assembled and after said thin tube is sealed at both ends, with said support introduced inside said thin tube and with said volume of substance received in said support, said sheathing self-immerses in the cryogenic agent without surface floating, including when said predetermined volume is a drop, further wherein said ballast weight has a weight that causes said sheathing, when in the cryogenic agent, to assume a vertical orientation by the effect of said ballast weight, with the one end of said sheathing vertically below the other end thereof, thus preventing residual air contained in said sheathing from causing said sheathing to float on the surface of the cryogenic agent, and further wherein said ballast weight is fabricated to have a given cross-sectional configuration.

2. The kit according to claim 1, wherein said ballast weight is disposed inside said thin tube.

3. The kit according to claim 2, wherein said ballast weight is a slug including a round cross section first portion and an oval cross section second portion (26).

4. The kit according to claim 2, wherein said ballast weight is a ball.

5. The kit according to claim 2, wherein said ballast weight abuts against a welded portion at one end of said thin tube.

6. The kit according to claim 2, characterized in that there exist between said ballast weight and said thin tube holding means for holding said ballast weight in said thin tube at a predetermined position.

7. The kit according to claim 6, wherein said holding means include at least one projecting portion of said ballast weight.

8. The kit according to claim 1, wherein said ballast weight is disposed around said thin tube.

9. The kit according to claim 8, wherein said ballast weight is a ring.

10. The kit according to claim 8, wherein said thin tube has a predetermined outside diameter (De) and said ballast weight has a predetermined inside diameter less than said outside diameter (De) of said thin tube by which said ballast weight is held in place by deforming said thin tube (6).

11. The kit according to claim 1, wherein said ballast weight is made of metal.

12. The kit according to claim 1, characterized in that means for identifying said biological substance are associated with said ballast weight.

13. The kit according to claim 12, wherein said identification means are visual.

14. The kit according to claim 12, wherein said identification means are electronic.

15. The kit according to claim 1, wherein said ballast weight gives said sheathing a heavier weight at the one end than at the other end.

16. The kit according to claim 2, wherein at least a portion of said ballast weight has a transverse dimension greater than the inside diameter of said thin tube.

17. The kit according to claim 1, wherein said ballast weight is fabricated to have a given length.

18. The kit according to claim 1, wherein said cross-sectional configuration is selected to cause said ballast weight to deform said thin tube when assembled to said thin tube.

* * * * *